United States Patent [19]

Gellert

[11] Patent Number: 4,475,911

[45] Date of Patent: Oct. 9, 1984

[54] ABSORBENT DEVICES

[75] Inventor: Dale A. Gellert, Aurora, Ind.

[73] Assignee: The Procter & Gamble Company, Cincinnati, Ohio

[21] Appl. No.: 253,426

[22] Filed: Apr. 13, 1981

[51] Int. Cl.³ .............................................. A61F 13/16
[52] U.S. Cl. .................... 604/367; 604/371; 604/375; 604/904
[58] Field of Search ............... 128/284, 287, 290 R, 128/290 P, 290 W, 296, 285; 604/367, 370, 371, 372, 904

[56] References Cited

U.S. PATENT DOCUMENTS

| | | |
|---|---|---|
| 2,178,704 | 11/1939 | Robinson . |
| 2,214,124 | 9/1940 | Dreyfus . |
| 2,716,449 | 9/1956 | Bletzinger . |
| 2,968,858 | 1/1961 | Brenner et al. . |
| 3,177,872 | 4/1965 | Pearman . |
| 3,287,222 | 11/1966 | Larde et al. . |
| 3,371,667 | 3/1968 | Morse ............................ 128/290 R |
| 3,399,672 | 9/1968 | Crowe, Jr. et al. . |
| 3,593,715 | 7/1971 | Merrill .............................. 128/285 |
| 3,703,897 | 11/1972 | Mack et al. . |
| 3,706,311 | 12/1972 | Kokx et al. . |
| 3,815,601 | 6/1974 | Schaefer . |
| 3,886,941 | 6/1975 | Duane et al. ................... 128/290 R |
| 4,023,571 | 5/1977 | Comerford et al. ............ 128/290 R |
| 4,319,956 | 3/1982 | Snyder et al. ....................... 128/296 |
| 4,324,247 | 4/1982 | Aziz .............................. 128/290 R |

Primary Examiner—C. Fred Rosenbaum
Assistant Examiner—Sherri E. Vinyard
Attorney, Agent, or Firm—Monte D. Witte; Fredrick H. Braun; Richard C. Witte

[57] ABSTRACT

Absorbent devices, such as catamenial tampons and catamenial pads. The devices comprise an unbonded array of non-absorbent, hydrophillic, resilient, moisture insensitive fibers contained within a porous overwrap. When the devices are intended to be presented in the compressed state, the compressed density of the mass of fibers should be less than about 0.3 grams per cubic centimeter. The devices can contain ancillary absorbent material.

3 Claims, 10 Drawing Figures

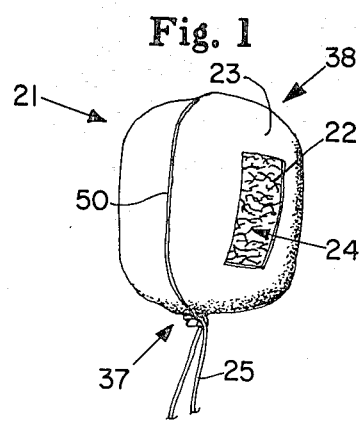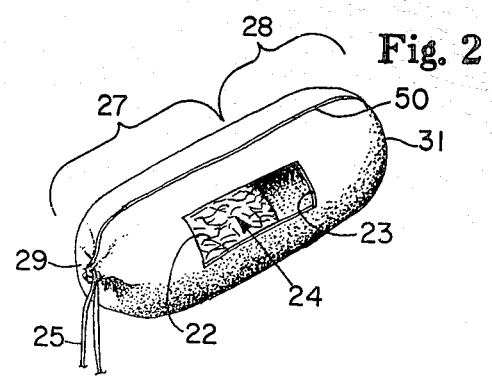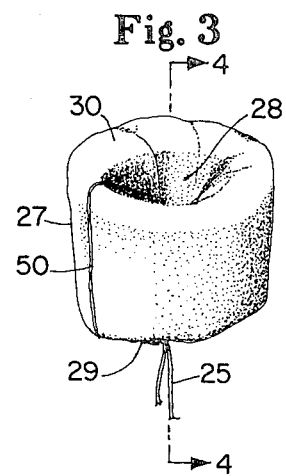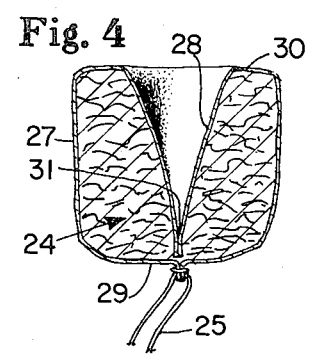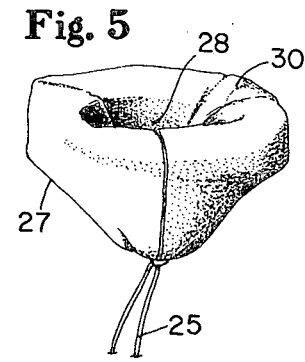

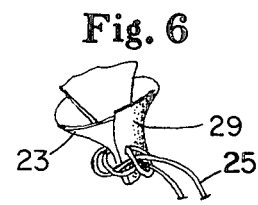
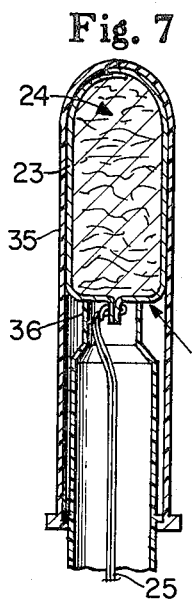
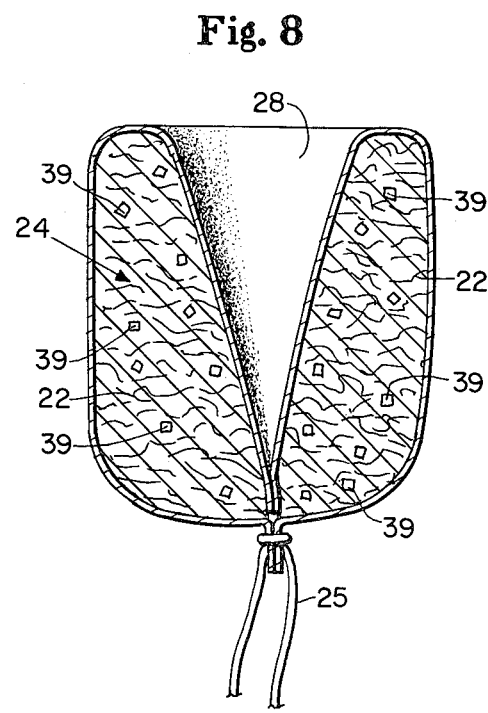

ABSORBENT DEVICES

BACKGROUND OF THE INVENTION

1. Field of the Invention

This invention generally concerns absorbent products designed to adsorb body fluids and, more particularly, catamenial tampons designed to be worn within the vagina while receiving catamenia of women and, most particularly, catemenial tampons having an absorbent body which comprises an unbonded array of non-absorbent, hydrophilic, resilient, moisture insensitive fibers contained within a relatively loose fitting, porous overwrap.

2. Background Art

Heretofore, catamenial tampons have been primarily of two basic types. The first type is a generally rigid, highly compressed, absorbent body composed of absorbent fibers. Normally these tampons are presented as highly compressed cylinders approximately 3.8 to 5 centimeters long and 1.2 centimeters in diameter. These tampons have been highly compressed to facilitate insertion into body cavities and expand, if at all, only when contacted by the fluid to be absorbed. This compressed construction leads to the creation of very small voids and fluid passageways having relatively high capillarity thereby causing rapid and directional fluid transport within the tampon. One result of this state of affairs is rapid wicking of absorbed fluids to the anterior or lowermost portion of such a tampon thereby leading to early in-use failure. Another defect of such tampons is their relatively low absorbent capacity caused by their relatively high densities even in view of the inherent absorbent nature of their fibrous components. Finally, such tampons typically exhibit low resiliency both wet and dry with a concomitant inability to conform to the vaginal walls thereby frequently allowing by-pass (i.e. non-absorption) of fluids.

The second type of tampon is well illustrated by Schaeffer in U.S. Pat. No. 3,815,601 which issued on June 11, 1974 and which is herein incorporated by reference. Schaeffer discloses an improved tampon comprising an absorbent body which is an aggregate of separate pieces of low modulous, resilient, absorbent foam. The aggregate is held together by a porous overwrap which fits relatively loosely about the aggregate to permit relative motion between adjacent pieces of the foam aggregate. This tampon establishes and maintains a relatively large volume within the vagina immediately upon insertion and, therefore, has a relatively greater absorbent capacity than the absorbent fiber tampons discussed above. In addition, the Schaeffer tampon expands to substantially fill the entire cross-section of the vagina and into substantially complete contact with the vaginal walls thereby providing improved containment of fluids and by-pass control as compared to the compressed absobent fiber tampons.

SUMMARY OF THE INVENTION

The present invention is a catamenial tampon comprising unbonded, non-absorbent, hydrophilic, resilient, moisture insensitive fibers contained within a relatively loose fitting porous overwrap. The tampon of this invention has the properties of being able to be compressed and contained within an inserter of convenient size, of being easily ejected from the inserter by application of only moderate force, of rapidly expanding to a relatively large volume without the presence of moisture, of rapidly absorbing relatively large quantities of fluids, and of being sufficiently resilient in both the dry and the moistened states to resist deformations induced by the wearer's movements and during withdrawal from the wearer's body.

BRIEF DESCRIPTION OF THE DRAWINGS

While this specification concludes with claims particularly pointing out and distinctly claiming the subject matter regarded as the invention, it is believed that the invention can be better understood from a reading of the following Detailed Description of the Invention and from reference to the accompanying drawings in which the thicknesses of some of the materials have been exaggerated for clarity and in which:

FIG. 1 is a perspective of a tampon of this invention with the overwrap partially cut away to permit illustration of the tampon interior;

FIG. 2 is a perspective of another embodiment of a tampon of this invention at one stage in its formation and wherein the overwrap is partially cut away for illustrative purposes;

FIG. 3 is a perspective view of the embodiment of FIG. 2 in its formed configuration;

FIG. 4 is a sectional view taken along line 4—4 of FIG. 3;

FIG. 5 is a perspective view of an alternate embodiment of a tampon of this invention;

FIG. 6 is an enlarged fragmentary perspective view illustrating the attachment of a withdrawal string to a tampon of this invention;

FIG. 7 is a cross-sectional view of the tampon of FIG. 1 and a telescoping tubular inserter; and FIG. 8 is a cross-sectional view, similar to FIG. 4, showing an alternate embodiment of a tampon of this invention.

DETAILED DESCRIPTION OF THE INVENTION

Figure 9:
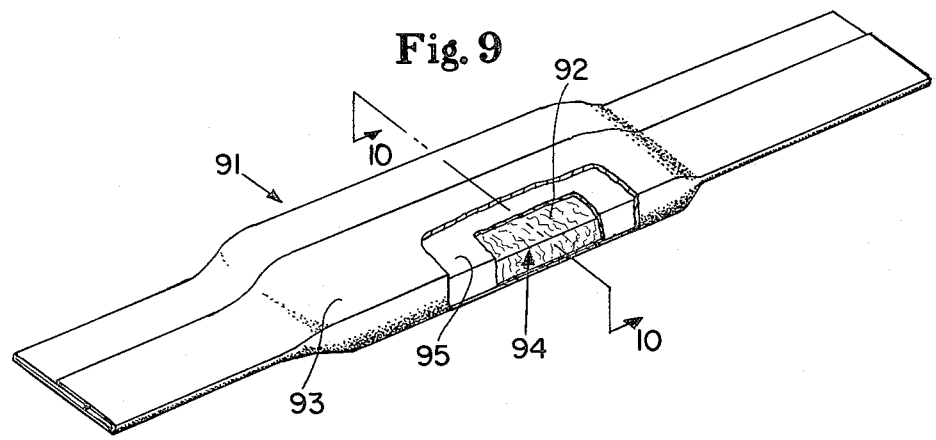
FIG. 9 is a perspective view of a catamenial pad of this invention with the topsheet and the backsheet partially cut away to permit illustration of the interior.

In general, the invention described herein is a catamenial tampon comprising unbonded, non-absorbent, hydrophilic, resilient, moisture insensitive fibers contained within a relatively loose fitting porous overwrap. While the invention is discussed in terms of catamenial tampons, it should be understood that other absorbent devices, such as tampons other than catamenial tampons, dental pads, surgical sponges, catamenial pads, diapers, and the like, can be based upon the same teachings presented for catamenial tampons and fall within the scope of the present invention.

The basis of the catamenial tampon of this invention (hereinafter sometimes referred to simply as "tampon") is an absorbent mass of fibers. It should be emphasized that it is the mass of fiber, not the individual fiber, which is absorbent.

The fibers comprising this absorbent mass must be non-absorbent, hydrophilic, resilient, and moisture insensitive.

As used herein, non-absorbent refers to the fact that the fibers do not absorb significant quantities of moisture within the fiber itself. It is to be recognized that virtually all materials will absorb some small quantity of moisture. A fiber is considered to be non-absorbent for present purposes if it will intrinsicly gain no more than about 6% in weight when a bone dry fiber is maintained at 21° C. and 65% relative humidity for 24 hours.

The fibers used in the tampon must have a surface which is mensephilic. That is to say, the fibers must have surface characteristics such that menstrual fluid tends to spread readily or spontaneously across their surfaces and, more importantly, into the capillaries formed between fibers in the absorbent mass. An alternate way of describing the fibers used in this invention is to say that their surfaces are wetted by menstrual fluid. Since menstrual fluid is primarily an aqueous solution, materials on which it spreads spontaneously can be loosely described as hydrophilic and the fibers used in the tampon have been so described supra.

The state of the art respecting wetting of materials allows a more precise description of hydrophilicity or wettability in terms of contact angles and surface tensions of the fluids and solids involved. This description is disclosed in detail in the American Chemical Society publication entitled *Contact Angle, Wettability and Adhesion*, edited by Robert F. Gould, and copyrighted in 1964, said publication being herein incorporated by reference.

Menstrual fluid normally has a surface tension of from about 35 to about 60 dynes per centimeter. It will have a contact angle of less than 90° and will tend to spread spontaneously on a solid which has a critical surface tension value greater than the fluid's surface tension. Since the surface tension of water is higher than that of menstrual fluid, any solid which is hydrophilic is also usually mensesphilic.

As noted supra, the basic teachings of this invention can be used to design and construct absorbent devices other than catamenial tampons. In such cases, the fluids absorbed will in general be other than menstrual fluids. The fibers used in such other devices must, then, be wetted by the fluid the devices are intended to absorb.

Unless otherwise indicated, the term hydrophilic is used herein to describe surfaces which are wetted by the fluid in question. A surface is said to be wetted by fluid either when the contact angle between the fluid and the surface is less than 90° or when the fluid will tend to spread spontaneously across the surface; both conditions normally co-exist.

The surface of the fibers used in the tampons can be rendered hydrophilic by any convenient means. For example, the material of construction of the fiber can itself be instrinsicly hydrophilic. Alternatively, the fibers can be provided with a finish during processing which renders their surfaces hydrophilic. Examples of such fibers with suitable commercial finishes are Type 101 polypropylene manufactured by Hercules, Inc. of Wilmington, Del. and the polypropylene fibers sold under the designation C-01-S-021 by Phillips Petroleum Corp. of Bartlesville, Okla.

A still further method of rendering the fiber surfaces hydrophilic is to treat the fibers with a surfactant as by spraying the fibers with the surfactant with or without an inert solvent; dipping the fibers into the surfactant; or contacting the fibers with an aqueous solution of the surfactant, separating the fibers and excess solution, and removing the water from the solution still associated with the fibers.

Examples of fibers which can be treated in this manner include those sold under the Orlon trademark (such as Type 72 Orlon) by E. I. DuPont de Nemours, Inc. of Wilmington, Del.; those sold under the Kevlar trademark by DuPont; and those sold under the Kodel trademark by Eastman Chemical Products, Inc. of Kingsport, Tenn., and polyester fibers.

Examples of surfactants which may be used to treat the surface of such fibers include nonionic and anionic materials. Specific examples include Pluronic L-92, a nonionic surfactant having a molecular weight of about 3,600 and a hydroxyl number of about 31, as made by BASF Wyandotte of Wyandotte, Mich.; and Plurocol Polyol 747, an ethylene oxide-propylene oxide block copolymer of pentaerythritol having an ethylene oxide content of 73% by weight and a hydroxyl number of 14, also made by BASF Wyandotte. (Hydroxyl number is defined as the number of milligrams of potassium hydroxide required to completely neutralize the hydrolysis product of the fully acylated derivative prepared from one gram of a material such as a polyhydroxy surfactant.) Another suitable material is Pluronic P-84, which is a nonionic surfactant prepared by condensing ethylene oxide with a hydrophobic base formed by condensing propylene oxide with propylene glycol and which is sold by BASF Wyandotte. A suitable anionic surfactant is a sodium salt of a fatty acid having from about 12 to about 18 carbon atoms.

The fibers used in the absorbent mass of the tampon must be resilient. Resiliency is the intrinsic property of a fiber which allows the individual fiber to resist physical deformation or, conversely, which causes the fiber to tend to reassume its original configuration after deformation such as elongation. The resiliency of fibers can be described by the initial modulus of the fibers. Initial modulus can be measured according to A.S.T.M. Standard Method D3822 (Standard Test Method for Textile Properties of Single Textile Fibers) which method is herein incorporated by reference. Initial modulus is measured in terms of grams per denier.

To be useful in the tampon, fibers should have an initial modulous greater than about 30 grams per denier.

The immediately preceding discussion of resiliency and modulus refers to the resilient properties of the dry fiber, properties which allow the tampon to expand spontaneously in the dry state when the tampon is released from a confining inserter. To be useful in the present invention, the fibers must also possess a high degree of wet resiliency. That is to say, the fibers must have an intrinsic ability to resist bending and to reassume their original configuration even when wetted since the tampon will be subjected to compressive and deforming forces in use and must resist such forces, must maintain its contact with the vaginal walls and must return to its original configuration when the forces are removed. Certain fibers, such as rayon fibers, have a high degree of resiliency in the dry state, but are essentially non-resilient when wetted. Such fibers are, in general, not useful in the present invention.

The term moisture insensitive is used herein to describe fibers whose resiliency is relatively unaffected by the presence of moisture. Fibers are said to be moisture insensitive when their initial modulous in the presence of moisture is at least about 90% of the initial dry state modulus.

Because the fibers used in the tampon are non-absorbent, menstrual fluid must be absorbed in the interstices, or capillaries, between fibers. Generally, in a random array of fibers, smaller fibers create a greater number of and larger overall volume of capillaries than do larger fibers and, therefore, provide a mass having a relatively greater absorption of fluids. Also, a relatively large number of smaller fibers are present in a mass of a given weight; this also leads to a greater number of capillary spaces between fibers and a greater overall surface area of fiber. Consequently, the fibers used in the tampon should have relatively small diameters in order to provide a greater number of capillary spaces and a greater surface area. Further, as described infra, the mass of fibers is contained within a porous overwrap. The porosity of the overwrap and the intrinsic resiliency of the fibers sometimes combine to allow individual fiber ends to protrude through the overwrap. In order to insure comfort to the wearer, these protruding fibers must be small enough in diameter so as to provide comfort comparable to that provided by the overwrap per se.

From the foregoing brief discussion, it should be apparent that the diameter of the fibers used in the tampon must be a compromise between competing effects. In general, fibers meeting the other criteria can have a diameter of from about 0.75 to about 6 denier and satisfy the requirements of this invention.

The length of the fibers used in this invention, just as is the diameter, is a compromise among several competing factors such as resiliency and number of fibers to provide a large number of capillaries. When the fibers meet the other criteria enumerated supra, a length of from about 0.60 to about 7.6 centimeters is generally satisfactory. Preferably, the fibers are on the order of 3.8 centimeters long.

Fibers suitable for use in the present invention can frequently be obtained in various shapes. Round and trilobal fibers are generally preferred to other shapes, although fibers of various shapes are useful.

Synthetic fibers useful in the present invention are frequently supplied as crimped fibers. Crimped fibers are required for use in the present invention. Degree of crimping is expressed by percent crimp which is defined as 100 times the quotient obtained when the difference between the fully extended length of a fiber and its relaxed crimped length is divided by its relaxed crimped length.

It is anticipated that the tampons will be provided to users in a compressed state and will be contained within an inserter as hereinafter described. A significant advantage of the tampons of this invention is their ability to spontaneously expand from a compressed configuration into a configuration conforming to the vaginal walls. It is, therefore, important that the fibers do not permanently assume their compressed configuration. If the fibers meet the modulus criteria described above, they will, in general, not be permanently deformed by the mere act of compression sufficient to place the tampon within an inserter. Some fibers, however, do tend to take a permanent deformation or "compression set" after being maintained in a compressed state for an extended period of time. This compression set is generally related to the glass transition temperature of the fibers. Fibers used in compressed tampons of this invention should have a glass transition temperature greater than about 30° C. Such fibers have good creep resistance under normal storage conditions.

Naturally, if the tampon, or other device, is not intended to be maintained in a compressed state for any extended period of time, the glass transition temperature of the fibers is relatively unimportant. It is only when the tampon or other device is intended to be maintained in a compressed state for an extended period of time that the glass transition temperature assumes importance. Polypropylene fibers are an example of fibers useful when the tampons or other devices will not be maintained in a compressed state for extended periods of time.

The fibers used in the tampon are generally randomly arrayed in the absorbent mass. That is to say, no conscious effort is made during manufacture to align the fibers in any regular or ordered array. In fact, it is necessary that the fibers generally do not have a regular, ordered arrangement. The hereinafter described techniques tend to insure a generally random array of fibers.

As noted supra, synthetic fibers useful in the present invention are frequently supplied in crimped form. Commercially available masses of crimped fibers are generally regularly arrayed or oriented. These masses should be disoriented ("opened" or "bloomed") before being made into the absorbent mass. Fibers can be opened by any of the techniques common in the fiber art such as those used in equipment made by Carolina Machinery Company of Charlotte, N.C. In general, any machine useful for preparing fibers for feeding to carding machines can be used.

When used in this invention, the absorbent mass of fibers should be unbonded. That is to say, the fibers should be free to move relative one to another under the influence of externally applied forces. It is anticipated that no binders or adhesives will be used although the fibers may intrinsicly exhibit some bonding forces such as van der Waals forces and although the fiber finishes or applied surfactants may impart some small amount of adhesiveness or cohesiveness to the fibers.

After opening, the fibers are normally in such a state ("fluffed") that they can be used in the tampons of this invention without further processing. An appropriate amount of fiber is segregated by any convenient means, and packed into the overwrap (described infra) by any convenient means. If desired, the fibers can be air laid by standard techniques to form an absorbent batt before the appropriate amount is segregated and packed.

The material used as the overwrap in this invention preferably is a soft, flexible, fluid permeable material.

Two nonwoven fabrics which will function as the overwrap are Dexter X-2172, a nonwoven fabric consisting of approximately a 60:40 cotton:rayon blend, saturation bonded with a mixture of HA8 and HA24, Rohm & Haas (Philadelphia, Pa.) acrylic binders, said fabric having a measured weight of from about 23.7 to 33.9 grams per square meter, being hydrophobic, and available from C. H. Dexter & Sons Co., Windsor Locks, Conn.; and Viskon, a nonwoven rayon, line-bonded, hydrophilic material having a measured weight of about 15.9 grams per square meter available from Chicopee Mills, New York, N.Y.

Reemay, a hydrophobic, spunbonded, low basis weight, polyester nonwoven fabric having a measured weight of about 13.5 grams per square meter and available from E. I. DuPont de Nemours, Wilmington, Del., is a nonwoven fabric which performs satisfactorily as an overwrap for the tampons.

The overwrap materials described immediately supra generally have small apertures therethrough. The presence of apertures is not necessary in the overwrap material so long as the overwrap material is permeable to menses. Should the overwrap be provided with apertures, the apertures should be small enough to essentially completely contain the fibers of the absorbent mass.

According to one view within the tampon industry, the overwrap should have a static coefficient of friction with the interior of the inserter of less than about 0.40, and preferably less than about 0.37, to provide acceptable ejection forces with larger tampons. Should fibers project through the overwrap, the nominal coefficient of friction between the overwrap/fiber combination and the interior of the inserter can be quite different from that between the overwrap per se and the inserter. The in-use friction between the overwrap/fiber combination and the inserter is the important consideration.

The overwrap should have strength characteristics so as to prevent the nonwoven material from rupturing during removal or from vaginal pressures while in vivo. The overwrap should have a wet tensile strength in the machine direction of at least about 230 grams per centimeter and in the cross direction of at least about 95 grams per centimeter. The minimum wet internal tearing resistance as measured by TAPPI Sandard T 414 ts-65 in the machine direction for the overwrap should be about 100 grams to tear 16 plies 5 centimeters to prevent the overwrap from tearing during removal of the tampon from the vagina.

A tampon 21 of this invention is shown in FIG. 1. It comprises an absorbent mass 24 of individual fibers 22 as hereinbefore described. Absorbent mass 24 is wholly encased within overwrap 23 and a withdrawal string 25 is securely attached to overwrap 23.

Any string sufficiently strong to withstand removal forces can be used as withdrawal string 25. One material which has worked well as a withdrawal string is a waterproofed cotton string having a 5/3 ply and a 4 kg tensile strength. Such a string is available from Bibb Manufacturing Company, Macon, Ga. under the name of 5/3 ply Sno-Spun bleach 108 cotton. Polyester strings generally have a higher tensile strength than do cotton strings and can be used if a stronger string is desired. Polyester strings are available from the Uni-Royal Fiber & Textile Division of UniRoyal, Inc., Winnsboro, S.C.

A tampon as shown in FIG. 1 can be made in the following manner. The overwrap can be formed from a rectangular piece of material described hereinbefore by bringing two opposite edges of the rectangular piece together to form a tube having a longitudinal seam such as seam 50 which is secured by any of several well known methods, such as sewing or gluing. One end of the formed tube can then be gathered radially inwardly and fastened to form a closure, such as distal end 37. This closure can be held by any of many various well known means such as sewing, gluing, or tying with a string. The overwrap at this stage is tubular with distal end 37 closed and proximal end 38 open. The fibers 22 comprising absorbent mass 24 then are placed within the bag formed by the ovewrap and proximal end 38 of the now tubular overwrap is gathered radially inwardly and fastened by any of several well known means such as gluing or sewing to form a closure so that the finished overwrap has both ends closed. Thus the overwrap is essentially tubular and the tampon cylindrical.

Withdrawal string 25 is attached to the overwrap because of the lack of tensile strength within absorbent mass 24 itself. Withdrawal string 25, of course, provides a means of withdrawing the tampon from the vagina after the tampon is soiled. It can be attached to or otherwise associated with overwrap 23 in many different ways, such as threading a doubled string through overwrap 23, preferably through a gathering of overwrap 23 such as may exist at the closed end, to form a loop and passing the free ends of withdrawal string 25 through the loop, such as is shown in more detail in FIG. 6; fixing withdrawal string 25 to the surface of overwrap 23 by sewing or bonding it thereto sufficiently to withstand forces encountered during withdrawal; and by tying withdrawal string 25 around a gathered end of overwrap 23. In a tampon of the structure of FIG. 4, i.e. one having a reentrant portion 28 of the overwrap, withdrawal string 25 can also be threaded, if desired, through reentrant end 31 to insure that reentrant end 31 remains adjacent closed end 29. (Reference numerals have the same meaning in each of the several figures.)

The expression "gathered" as used herein is intended to include any bringing together of the overwrap at a longitudinal end to form a closure of the overwrap at that end, e.g. a closure in which the overwrap is omnidirectionally gathered radially inwardly, as if drawn by a drawstring; a fin seal wherein the terminal end is flattened to a single plane by forces perpendicular to the plane; a lapped joint wherein the terminal end is folded inwardly and diametric portions of the end overlap, etc. A terminal end of the overwrap or any portion of the overwrap can be any extremity or margin of the overwrap, such as is indicated by end 31 in FIG. 2.

Referring now to FIG. 3, an alternate embodiment tampon of this invention (hereinafter referred to as "rosette") is shown which has a cavity therein formed by a reentrant portion 28 of the overwrap. The tubular shaped overwrap used for the rosette is longer than overwrap 23 of FIG. 1 and it comprises an exterior portion 27 and a reentrant portion 28 as indicated in FIG. 2. Distal end 29 of the rosette is gathered and secured by any of the means well known for forming a closure, for example, sewing or gluing the gathered end. The overwrap is about twice as long as overwrap 23 for the tampon of FIG. 1, and exterior portion 27 and reentrant portion 28 each are about 50 percent of the length of the tubular overwrap. The absorbent mass of fibers is placed within the overwrap and, depending upon the amount used (as hereinafter described) the absorbent mass may or may not completely fill out the overwrap. The terminal end of reentrant portion 28 at reentrant end 31, as shown in FIG. 4, of the overwrap can be, but does not necessarily have to be, gathered and closed. Reentrant portion 28 is folded inwardly along the longitudinal axis of the tampon and the absorbent mass is shaped to form the cavity in the tampon of FIG. 3. The surface of the cavity within the tampon is formed by reentrant portion 28, i.e., reentrant portion 28 is folded around cavity end 30 of the absorbent mass and inwardly through the absorbent mass to form the rosette structure. This structure is shown in cross-section in FIG. 4 wherein reentrant end 31 is adjacent to closed end 29. Thus there is formed a tampon wherein the absorbent mass 24 of fibers is encased by an overwrap having an exterior portion 27 forming the exterior surface of the tampon and a reentrant portion 28 forming the surface of the cavity. A withdrawal string 25 can be attached as described above.

The embodiment shown in FIG. 5 is another rosette, similar to that of FIG. 3, in that it has the absorbent mass enclosed by an overwrap having an exterior portion 27 and a reentrant portion 28, but the shape of the overwrap before the reentrant portion is tucked inwardly is essentially that of two truncated cones joined at their large bases. Thus the embodiment of FIG. 5 is generally conically shaped and has a cavity. Also, it can have a withdrawal string 25 attached as has been described above.

The rosette shape is advantageous because its lateral spread when subjected to a force normal to the tampon's longitudinal axis is greater than the lateral spread of a tampon without a cavity in the middle, e.g., a cylindrical tampon. The greater lateral spread is beneficial because the vagina exerts a normal force on the tampon causing the tampon to spread outward toward the lateral walls of the vagina and the spreading prevents menses from bypassing the tampon. Another advantage of the rosette shape is that it provides a larger periphery for a given amount of absorbent mass than a tampon without a cavity therein.

The tampon of this invention can be inserted into a vagina via a telescoping tube type inserter, as is well known to those of ordinary skill in the tampon art. One such inserter having inwardly tapering flexible segments at the leading end to form a normally closed, smooth, openable, leading end is shown in cross section in FIG. 7 with the tampon 21 of FIG. 1 held therein. The inserter can be molded from polyethylene or any of the other materials well known to those of ordinary skill in the tampon inserter art. Tampon 21 is resiliently compressed and maintained in that condition before and during insertion by having been placed in the tubular inserter 35. Resiliently compressed as used herein means compressed to a degree such that the absorbent body takes on a readily releasable temporal set, i.e., a set which dissipates in the absence of liquids or moisture after the tampon is ejected from a constraining means such as an inserter. Overwrap 23 of tampon 21 is in contact with the inner surface of inserter 35. An ejecting means, such as the ejector 36, removes tampon 21 from the inserter. In the embodiment of FIG. 7, ejector 36 pushes against the rear end of tampon 21 to move it forward in the inserter where it opens the closure at the forward end of inserter 35 and is expelled from inserter 35.

The tampon, in the inserter shown, forces open the segments at the forward end of the inserter. Inserter 35 is inserted into the vagina and tampon 21 is ejected from the outer tube by pushing ejector 36 so that it telescopes within inserter 35. Inserter 35, with ejector 36 therein, is removed from the vagina after tampon 21 has been fully ejected from inserter 35 and deposited within the vagina.

An alternate embodiment of the tampon of this invention is shown in FIG. 8 wherein pieces 39 of ancillary absorbent material are distributed within absorbent mass 24 of fibers 22.

Many different ancillary absorbent mateials can be used for various purposes. One of these purposes is to hold liquids within the absorbent mass after they have been absorbed to reduce squeeze-out as when a liquid-loaded tampon is compressed. An ancillary absorbent material which will perform satisfactory in the tampon of this invention is cross-linked carboxymethyl cellulose such as that disclosed in U.S. Pat. No. 3,589,364 issued to Dean et al. on June 29, 1971, which patent is herein incorporated by reference.

A preferred ancillary absorbent material is the essentially acidic carboxymethyl cellulose described in U.S. Pat. No. 3,678,031 issued to Schoggen on July 18, 1972, which patent is herein incorporated by reference.

Other ancillary absorbent materials which can be used include without limitation primarily insoluble carboxymethyl cellulose, polyacrylamides (primarily cross-linked), and starch derivatives, all of which are well-known to those of ordinary skill in the art. Of course, there are many other ancillary absorbent materials which can be included in the tampon and none are disclaimed.

The pieces 39 of ancillary absorbent material included in the tampon can be of many various sizes, shapes, and forms and can be located in various positions within the tampon. In a preferred embodiment, pieces 39 are small regular parallelepipeds cut from a sheet of essentially acidic carboxymethyl cellulose. These pieces 39 are then substantially uniformly distributed throughout absorbent mass 24. The percentage, by weight, of pieces 39 based on absorbent mass 24 ranges from about 10 percent to about 50 percent, preferably from about 15 percent to about 50 percent.

Alternate forms to the small pieces 39 of the ancillary absorbent material are pellets and individual fibers. Thin rods or bars of the ancillary material can also be used. These alternate forms of the pieces 39 can be located in many positions within the absorbent body of the tampon, such as uniformly distributed throughout the absorbent mass 24, as shown in FIG. 8, or concentrated in particular positions in the absorbent mass 24, such as near reentrant portion 28 of the overwrap.

The ancillary absorbent material can also be present in the form of a powder more or less uniformly distributed throughout the absorbent mass of fibers.

Preferably, ancillary absorbent material is used in the tampon of this invention. The presence of such material is particularly advantageous when the tampon of this invention is subjected to extreme conditions of menstrual fluid loading (such as occurs when the tampon is worn for long periods of time) or to extreme conditions of applied pressure (such as when the wearer is engaged in vigorous physical activity and when the tampon is removed).

The fit of overwrap 23 about absorbent mass 24 is preferably loose to a degree rather than tight. A loose overwrap makes the tampon look and feel fluffy and soft. A tight overwrap could restrict dry expansion of the tampon.

Preferably, the tampon, which expands spontaneously in the dry state when the confirming forces, as of the inserter, are removed, will occupy an expanded volume of from about 12 to about 25 cubic centimeters (cc) depending on the size of the tampon desired and the total absorbent capacity desired. As commonly available in the trade, super size tampons have an expanded volume of about 20 to 25 cc, regular about 16 to 17 cc, and moderate about 12 to 13 cc. The fit of the overwrap about the absorbent mass should be such that the overwrap will not restrict the expansion of the tampon to its maximum desired volume.

The quantity of fibers used in the tampon is an important parameter of this invention. The quantity of fibers present must be sufficient to provide adequate absorbency, but must not be so great as to hinder the dry expansion of the absorbent mass as the compressive forces are released. It has been found that dry expansion of the tampon is unduly restricted or hindered when the tampon must be compressed (so that, for example, it can be confined within an inserter) to such an extent that the compressed density of the absorbent mass is greater than about 0.3 gram per cubic centimeter (g/cc). Preferably, the length of the compressed tampon within the inserter, as generally illustrated in FIG. 7, is from about 5.1 to about 6.1 cm. The diameter of the compressed tampon within the inserter is from about 1.8 to about 1.3 cm. When the preferred polyester fibers are used, a super tampon will contain about 1.6 g fiber, a regular from about 1.2 to about 1.3 g, and a moderate from about 0.8 to about 1 g.

The preceding discussion has been directed to catamenial tampons. As noted in the "Background of the Invention" section of the specification, the present invention generally concerns absorbent products designed to absorb body fluids. As noted at the beginning of the "Detailed Description of the Invention" section, catamenial pads are absorbent devices which can be based on the teachings of this invention.

For example, catamenial pads can comprise an absorbent mass of fibers as hereinbefore described encased between a fluid permeable, user-contacting topsheet and a fluid impermeable backsheet. Optionally, the absorbent mass of fibers can contain an ancillary absorbent material as hereinbefore discussed. Optionally, the catamenial pads can be provided with means, such as adhesive tapes, for attachment to the users' undergarments.

In catamenial pads, the fibers used to form the absorbent mass must be the non-absorbent, hydrophilic, resilient, moisture insensitive fibers hereinbefore discussed. These fibers must have all the noted properties and characteristics.

The absorbent mass of fibers in the catamenial pad can be prepared as the absorbent mass is prepared for catamenial tampons. Typically, the absorbent mass of fibers will be generally rectangular or oval in shape, from about 17 to about 23 centimeters long and from about 5 to 7 centimeters wide. The quantity of fibers in the absorbent mass should be sufficient to contain a useful quantity of fluid. It is anticipated that the catamenial pads will be supplied to the user in a compressed state so that storage volume will be at a minimum. In this situation, the amount of fibers present in the absorbent mass should not be so great that the compressed density of the absorbent mass is greater than about 0.3 gram per cubic centimeter.

The topsheet can be any fluid permeable, preferably hydrophobic, material commonly used as topsheets in catamenial pads or disposable diapers such as carded, spunbonded, melt blown, or airlaid webs of natural or synthetic fibers or apertured or embossed and apertured continuous films.

One preferred topsheet comprises an apertured hydrophobic film (such as a thermoplastic such as polyethylene) having a caliper of less than about 0.075 centimeter, an open area of at least about 35%, and being provided with irregular apertures less than about 25% of which have an equivalent hydraulic diameter smaller than or equivalent to 0.064 centimeter. (Equivalent hydraulic diameter is defined as four times the quotient of the area of the aperture divided by its perimeter.) Optionally, the surface of the topsheet oriented toward the absorbent mass is provided with a thin layer of uniformally distributed fibers, such as polyester, nylon, rayon, or cotton fibers, which are preferably less hydrophobic than the topsheet. Optionally, and preferably, an additional element comprising a unidirectionally fluid permeable film provided with tapered capillaries as described in U.S. Pat. No. 3,929,135 which was issued to Thompson on Dec. 30, 1975 (which patent is incorporated herein by reference) is interposed between the topsheet and the absorbent mass.

The backsheet can be any conventional fluid impervious material used in catamenial pads and disposable diapers, such as a film prepared from a thermoplastic such as low density polyethylene.

In another embodiment, the catamenial pad can comprise an absorbent mass of fibers as hereinbefore described encased within a homogeneous outerwrap. The outerwrap is such that it functions both as a fluid pervious topsheet and a fluid impermeable backsheet. The outerwrap is manufactured from a fluid impermeable material such as a thermoplastic (for example, polyethylene) film and is provided with a multiplicity of protuberances projecting from the plane of the outerwrap toward the absorbent core and having a base in the plane of the outerwrap and an apex remote therefrom. Both the apex and the base of each protuberance are apertured. The openings may be circular, elliptical, or irregularly shaped. Preferably, the maximal diagonal of the largest apex opening is from about 0.025 centimeter to about 0.25 centimeter. (For rectilinear shapes, the maximal diagonal is the longest line that can be drawn between two nonadjacent verticies of the shape. For curvilinear shapes, the maximal diagonal is the largest diameter of the shape.) The maximal diagonal of the base openings is equal to or greater than the maximal diagonal of the apex opening. The protuberances may be formed by using any of several different methods well known to the art. For example, the apparatus disclosed in U.S. Pat. No. 4,151,240 which issued to Lucas et al on Apr. 24, 1979 (which patent is incorporated herein by reference) may be used. The caliper (i.e., the use thickness of the sheet after the protuberances have been formed as measured from the base to the apex of the protuberance) can be from about 0.033 centimeter to about 0.089 centimeter.

The actual design and method construction of the catamenial pad can correspond to any convenient design and method well known to those skilled in the art.

Figure 10:
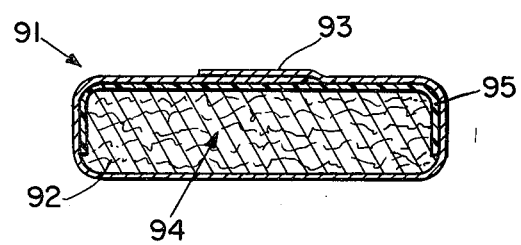
FIG. 10 is a sectional view taken along line 10—10 of FIG. 9.

One embodiment of the catamenial pad is shown in FIGS. 9 and 10. Absorbent mass 94 is shown to comprise individual fibers 92. Absorbent mass 94 is the absorbent mass prepared for catamenial tampons as described hereinbefore. As illustrated, absorbent mass 94 is generally rectangular in shape. Absorbent mass 94 is encased between topsheet 93 and backsheet 95.

The following examples are presented by way of illustration and not by way of limitation.

EXAMPLE I

Two hundred grams of Polyester fibers sold by E. I. du Pont de Nemours & Co. under the designation type 54 W Dacron, having a cut length of about 3.8 centimeters, being about 1.5 denier, and having about 45% crimp were washed according to the following scheme. (It should be noted that washing of the fibers is not normally considered to be a necessary step in the process of making the tampons of this invention. The particular fibers used in this example were commercially available fibers having an unknown, to the inventor, finish applied thereto. It was deemed expedient to remove the unknown finish and then to treat the fibers as noted hereinafter to render the fiber surfaces hydrophilic. It is to be expected that fibers will be available commercially either having the desired finish thereon or being completely free of finish. In the event that it is not possible to obtain fibers having the proper finish and surface characteristics, the fibers will be preferably washed prior to further processing and incorporation into tampons.)

The fibers were washed with a solution prepared by mixing 40 milliliters of a 5% by weight solution of Pluronic P-84 polyol dissolved in distilled water and 40 grams of a 5% solution of tetrasodium pyrophosphate dissolved in distilled water, with 3,920 milliliters of distilled water. (Pluronic P-84 polyol was used in this instance as a surfactant for removing the existing finish on the fibers; it was not used to impart a hydrophilic surface to the fibers.) The fibers were agitated in the wash solution for 30 seconds and then allowed to soak for an additional 270 seconds. The liquid and the fibers were separated and the fibers were manually compressed to remove excess liquid until the total weight of a moist fiber mass was less than about 800 grams. The moist fibers were subjected to a rinse operation by being placed in 4 liters distilled water and being agitated for 30 seconds. The fibers were then allowed to soak in the distilled water for an additional 270 seconds. Liquid and fibers were separated and the fibers were manually compressed to remove excess liquid until the moist fiber mass had a total weight of less about about 800 grams. The rinse operation was repeated 3 additional times to provide a total of 4 rinse operations. At the end of the fourth rinse operation, the fibers were manually compressed to remove liquid until the moist fiber mass weighed less than about 500 grams.

The washed fibers were than treated to provide them with a hydrophilic surface in the following manner. A 10% by weight solution of Plurocol 747 was prepared by dissolving the Plurocol 747 in a 50% by weight solution of ethanol. A treatment solution was prepared by mixing 40 milliliters of the Plurocol 747-ethanol solution, 980 milliliters of distilled water, and 980 milliliters of ethanol. (The ethanol used throughout this example was that known in the trade as 3A alcohol.) The 200 grams of dry fibers which have been washed as hereinbefore described, were placed in the treatment solution and agitated for three minutes. The fibers were separated from the treatment solution by vacuum filtration with a common Buchner funnel and the use of a rubber dam. The fibers were tedded and dried at ambient conditions.

The dried fibers were then opened (disoriented) by subjecting 10 grams aliquots to from about 4 to about 6 passes through a bench-scale textile carding machine made by Curtis Fricke of Granite Falls, Wash. Individual aliquiots weighing 1.35±0.05 grams were manually separated from the opened mass of fibers and manually mixed with 0.65±0.05 gram of essentially acidic carboxymethyl cellulose marketed by the Buckeye Cellulose Corporation, Memphis, Tenn., under the tradename CLD-2. The CLD-2 was presented as discrete particles which were generally regular parallelopipeds having edges about 0.24 cm, 0.24 cm, and 0.08 cm long, respectively.

The fibers and the ancillary absorbent material were then made into tampons of the rosette shape described hereinbefore and illustrated by FIG. 3. They were packed into a bag formed from the hereinbefore described Reemay fabric, the bag being approximately 18.1 centimeters in circumference and approximately 13.6 centimeters in length and sealed with 0.025 gram commercially available hot melt glue. One end was sutured with a five-strand polyester withdrawal string. The bag was then sewn shut at the open end and inverted to form the rosette shape. The finished tampon was compressed and placed in a plastic inserter having an inside diameter of approximately 1.66 centimeters.

On removal from their inserters, the tampons spontaneously expanded to an average dry volume of about 22 cc. Static head syngina absorbency with synthetic menstrual fluid of the tampons was, on the average, 21.3 grams.

The syngina is a well known artificial device used to simulate a vagina and to measure the absorbency of catamenial products such as tampons. It consists of a thin rubber membrane which holds the tampon, the membrane itself being enclosed within an outer case in such a way that water can be introduced between the membrane and the outer case to provide a hydraulic head on the exterior of the membrane. The syngina is so constructed that the hydraulic head can be maintained constant or can be varied at a regular cyclical rate. In the static head syngina test, the hydraulic head is maintained constant at about 18 centimeters of water. A tube is provided into the membrane at its anterior end so that synthetic menstrual fluid can be introduced to the product contained within the membrane. Synthetic menstrual fluid has a density, viscosity, and salinity equivalent to that of natural menstrual fluids. A reservoir of synthetic menstrual fluid is connected to the tube projecting within the syngina through a regulator such that the synthetic menstual fluid can be admitted to the interior of the syngina at a known rate. In the test used in this example, synthetic menstrual fluid was admitted to the syngina at a rate of 2 grams per minute. The absorbent capacity of the test sample was determined by measuring (by weight) the quantity of synthetic menstrual fluid absorbed by the product before the first quantity of synthetic menstrual fluid was visually observed to pass through or around the test product.

EXAMPLE II

Polyester fibers made by Celanese Corporation and sold under the designation D-227 were made into tampons according to the procedure of Example I. These particular fibers were 1.5 denier, were approximately 3.8 centimeters long, were trilobal in cross section, and were crimped to the extent of about 50%. The washing procedure, however, was as follows: Two hundred grams of fibers were washed four times, with 3.78 liters of isopropanol at room temperature. Each time the fibers were separated from the isopropanol by vacuum filtration in a Buchner funnel. These isopropanol washed fibers were then washed through three cycles in a commercial washing machine, each cycle comprising 5 water washes and 3 centrifugal separation cycles. (The water temperature was approximately 38° C.) One hundred grams of washed and air dried fibers were treated with a solution consisting of 2 grams L-92 surfactant, 500 milliliters ethanol, and 500 milliliters distilled water by agitating for 3 minutes at room temperature. Excess liquid was removed with a laboratory Buchner funnel and the fibers were allowed to air dry. Tampons made as in Example I had, on removal from the inserters, a dry volume of approximately 22 cc and an absorbent capacity of about 21.9 grams.

EXAMPLE III

Poly(cyclohexane dimethanol terephthalate) fibers sold by Eastman Chemical Products, Inc. under the tradename Kodel 211, being 3 denier, about 3.8 centimeters long, round, and crimped to the extent of about 45%, were washed as in Example II. They were then made into fibers as in Example I. On removal from the inserters, these tampons had an average dry volume of about 25 cc and an average absorbent capacity of about 26 grams.

What is claimed is:

1. A catamenial pad comprising an absorbent, unbonded array of fibers encased between a fluid pervious topsheet and a fluid impervious backsheet wherein said fibers are non-absorbent, hydrophilic, resilient, moisture insensitive, from about 0.75 to about 6 denier, from about 0.6 to about 7.6 centimeters long, and are crimped; and wherein said topsheet comprises an apertured hydrophobic film having a caliper less than about 0.075 centimeter and an open area of at least about 35% wherein less than about 25% of said apertures have an equivalent hydraulic diameter less than or equal to about 0.064 centimeter.

2. A catamenial pad comprising an absorbent, unbonded array of fibers encased within a homogeneous outerwrap wherein said fibers are non-absorbent, hydrophilic, resilient, and moisture insensitive and wherein said outerwrap comprises a fluid impermeable film provided with a multiplicity of protuberances having a base in the plane of said outerwrap and an apex remote therefrom, wherein said apex and said base are provided with openings, wherein the maximal diameter of the opening in said apex is less than about 0.25 centimeter and the maximal diameter of the opening in said base is at least as great as said maximal diameter of the opening in said apex.

3. The catamenial pad of claim 2 wherein said fibers are from about 0.75 to about 6 denier, are from about 0.6 to about 7.6 centimeters long, and are crimped.

* * * * *